(12) United States Patent
Serra et al.

(10) Patent No.: US 6,591,669 B1
(45) Date of Patent: Jul. 15, 2003

(54) APPARATUS FOR EXPERIMENTALLY MEASURING THE INTERACTION BETWEEN SURFACES AND RUBBER SPECIMENS

(75) Inventors: Antonio Serra, Genoa (IT); Alessandro Volpi, Milan (IT)

(73) Assignee: Pirelli Pneumatici S.p.A., Milan (IT)

( * ) Notice: Subject to any disclaimer, the term of this patent is extended or adjusted under 35 U.S.C. 154(b) by 0 days.

(21) Appl. No.: 09/603,908

(22) Filed: Jun. 26, 2000

Related U.S. Application Data
(60) Provisional application No. 60/145,273, filed on Jul. 26, 1999.

(30) Foreign Application Priority Data

Jun. 26, 1999 (EP) .............................. 99202074

(51) Int. Cl.[7] ........................ G01M 17/02; G01N 19/02
(52) U.S. Cl. ................................................ 73/146; 73/8
(58) Field of Search ............................ 73/146, 8, 146.2

(56) References Cited

U.S. PATENT DOCUMENTS

| | | | | |
|---|---|---|---|---|
| 1,490,899 A | * | 4/1924 | Scott ........................ 324/772 |
| 3,543,576 A | * | 12/1970 | Bishop ........................ 73/146 |
| 3,788,137 A | | 1/1974 | Lyon et al. |
| 3,895,518 A | * | 7/1975 | Leblond ....................... 73/146 |
| 3,948,095 A | * | 4/1976 | Burgett et al. ............... 73/146 |
| 4,038,863 A | | 8/1977 | Mellor et al. |
| 4,171,641 A | * | 10/1979 | Landsness ................... 73/146 |
| 4,238,954 A | * | 12/1980 | Langer ........................ 73/146 |
| 4,366,707 A | * | 1/1983 | Jarschel ....................... 73/146 |
| 4,593,557 A | * | 6/1986 | Oblizajek et al. ............ 73/146 |
| 4,704,900 A | * | 11/1987 | Beebe .......................... 73/146 |
| 5,281,003 A | * | 1/1994 | Herman ...................... 301/2.5 |
| 5,481,907 A | | 1/1996 | Chasco et al. |
| 5,689,058 A | * | 11/1997 | Yuan ............................... 73/9 |
| 5,767,402 A | | 6/1998 | Sandlass et al. |

FOREIGN PATENT DOCUMENTS

GB          2 104 010          3/1983

* cited by examiner

Primary Examiner—Hezron Williams
Assistant Examiner—Lilybett Martir
(74) Attorney, Agent, or Firm—Finnegan, Henderson, Farabow, Garrett & Dunner, L.L.P.

(57) ABSTRACT

The invention relates to an apparatus (1) for testing tire compounds, which comprises a road drum (3) and a specimen (5), rotating about respective parallel axes (X, Y) and being in rolling contact with each other.

The specimen (5) of rubber to be analysed is mounted at the end of a spindle operated by a motor (6): advantageously the spindle is housed inside a closed casing (63) so as not to be exposed to water or other agents during the tests.

This results in an apparatus wherein the spindle driving the specimen may be supported by non-sealed and hence low-friction bearings, thereby not altering the results of the tests carried out.

9 Claims, 4 Drawing Sheets

APPARATUS FOR EXPERIMENTALLY MEASURING THE INTERACTION BETWEEN SURFACES AND RUBBER SPECIMENS

This application claims the benefit of U.S. Provisional Application No. 60/145,273 filed Jul. 26, 1999, the content of which is incorporated herein by reference.

BACKGROUND OF THE INVENTION

The invention relates to those apparatuses which in the tire industry are used to test the behaviour of the rubber compounds, in connection with their rolling on surfaces with different morphological characteristics.

The apparatuses considered in the present description essentially consist of a so-called "road drum", namely a motorised cylindrical drum with a diameter of the order of 70–100 cm, on which a roller of smaller dimensions (generally with a diameter not greater than ⅕th of the road drum) constituting the specimen and having a radially external portion that over a thickness of preferably not less than 2 mm, is made with the vulcanized compound to be examined.

Also the specimen is driven and causing it to roll about the road drum, it is possible to analyse the behaviour of the compound being examined according to different operating situations which can be simulated with the apparatus, for example with relative slipping and/or with set drift angles.

In this manner it may be studied the behaviour of a compound under conditions of pure rolling contact between road drum and specimen or when there is relative slipping between them or when the inclination of the specimen with respect to the road drum is such as to reproduce the conditions to which the compound of a tire tread is subject during bends.

Furthermore, in some more complex machines, the tests may be performed by spraying water, dust and/or other elements in the zone where there is contact between the drum and specimen, thus fully simulating those situations which may occur in reality.

The present invention is based on the Applicant's realisation that, precisely in such a context, the apparatuses known hitherto are not satisfactory.

Indeed, it must be taken into account that the roller which forms the specimen to be tested is usually mounted on the end of a spindle rotating about an axis parallel to that of the road drum.

This spindle is operated in a manner known per se, at the opposite side with respect to the specimen; however, in order to operate it in an environment which is exposed to water or the other elements mentioned above, some precautions are required: the latter include the use of sealed bearings.

These bearings, however, produce an inevitable friction which is opposite to the rotation of the spindle, thereby altering significantly the measurements performed; this is the case in particular of the evaluation of the torques acting with respect to the axis of rotation of the spindle.

The object of the present invention is therefore that of providing an apparatus for testing rubber-compound specimens of tires, having structural and operational characteristics such as to overcome the drawbacks mentioned.

SUMMARY OF THE INVENTION

According to a first aspect, the invention relates to an apparatus for testing tire compounds, comprising a road drum and a specimen rotating about respective parallel axes and in rolling contact with each other, driving means for rotation of the road drum and the specimen, characterized in that these means comprise a specimen driving group in which there is a spindle driven by a motor, wherein the spindle is rotatably housed in a casing and the motor is fixed in a cradle seat integral with the casing so as to form a rigid body therewith, this body being supported in an idle manner with respect to the axis of rotation of the specimen.

Further characterising features of such an apparatus are set out in the claims which will follow.

BRIEF DESCRIPTION OF THE DRAWINGS

The invention will be understood more clearly in the light of the description which is provided below, relating to a preferred but not limiting embodiment illustrated in the accompanying drawings, wherein.

DETAILED DESCRIPTION OF THE PREFERRED EMBODIMENTS

Figure 1:
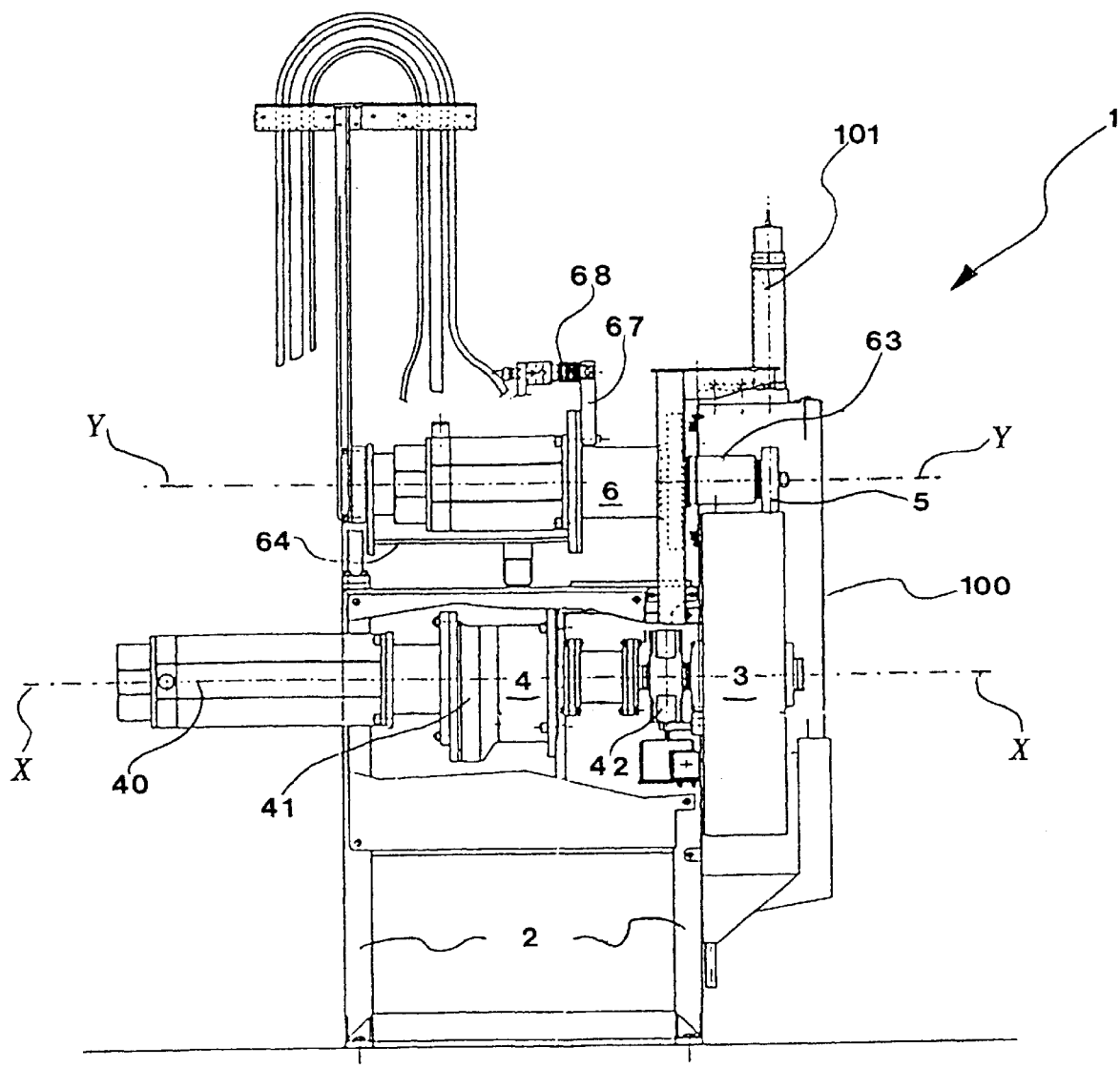
FIG. 1 shows a side view, with a removal part, of an apparatus according to the invention.

With reference to these drawings, numeral 1 indicates the whole apparatus according to the invention.

Said apparatus comprises a supporting structure 2 formed by a series of uprights and cross-pieces which support a road drum 3 with the associated driving group 4 active about an axis of rotation X, and a specimen 5 driven by a group 6 active with respect to the axis of rotation Y.

In accordance with a preferred embodiment, the external surface of the road drum 3 is divided up into circumferential bands (in this case three, the paths thereof are indicated by broken lines in FIG. 2) which have different degrees of roughness for the reasons that will emerge more clearly below.

The driving group 4 of the road drum 3 comprises an electric motor 40 of the brushless type, a reduction gear 41 and a braking device 42, which are all aligned along the axis X.

Figure 2:
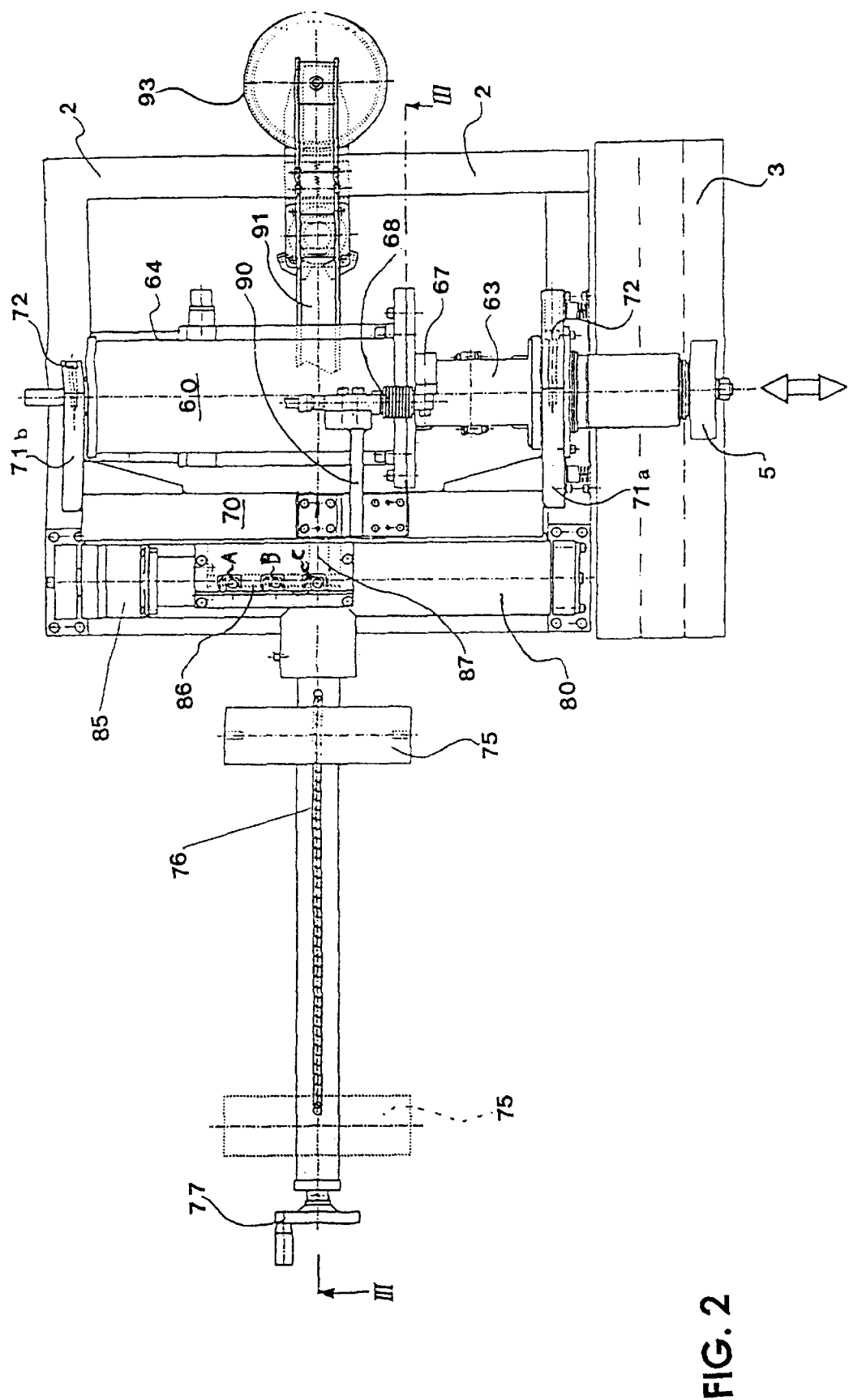
FIG. 2 shows a plan view of the apparatus of FIG. 1.
Figure 3:
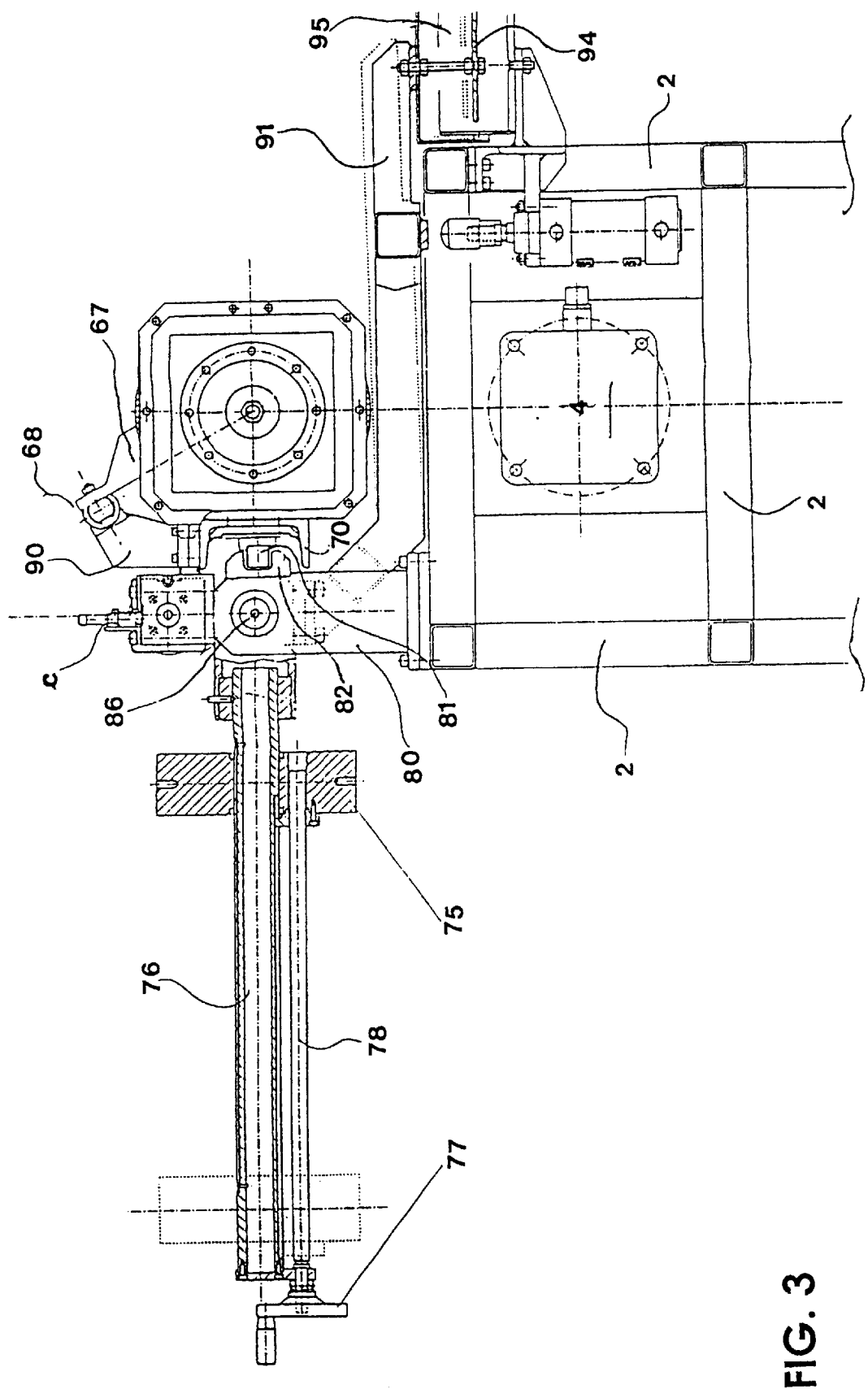
FIG. 3 shows a view sectioned along the line III—III in FIG. 2.
Figure 4:
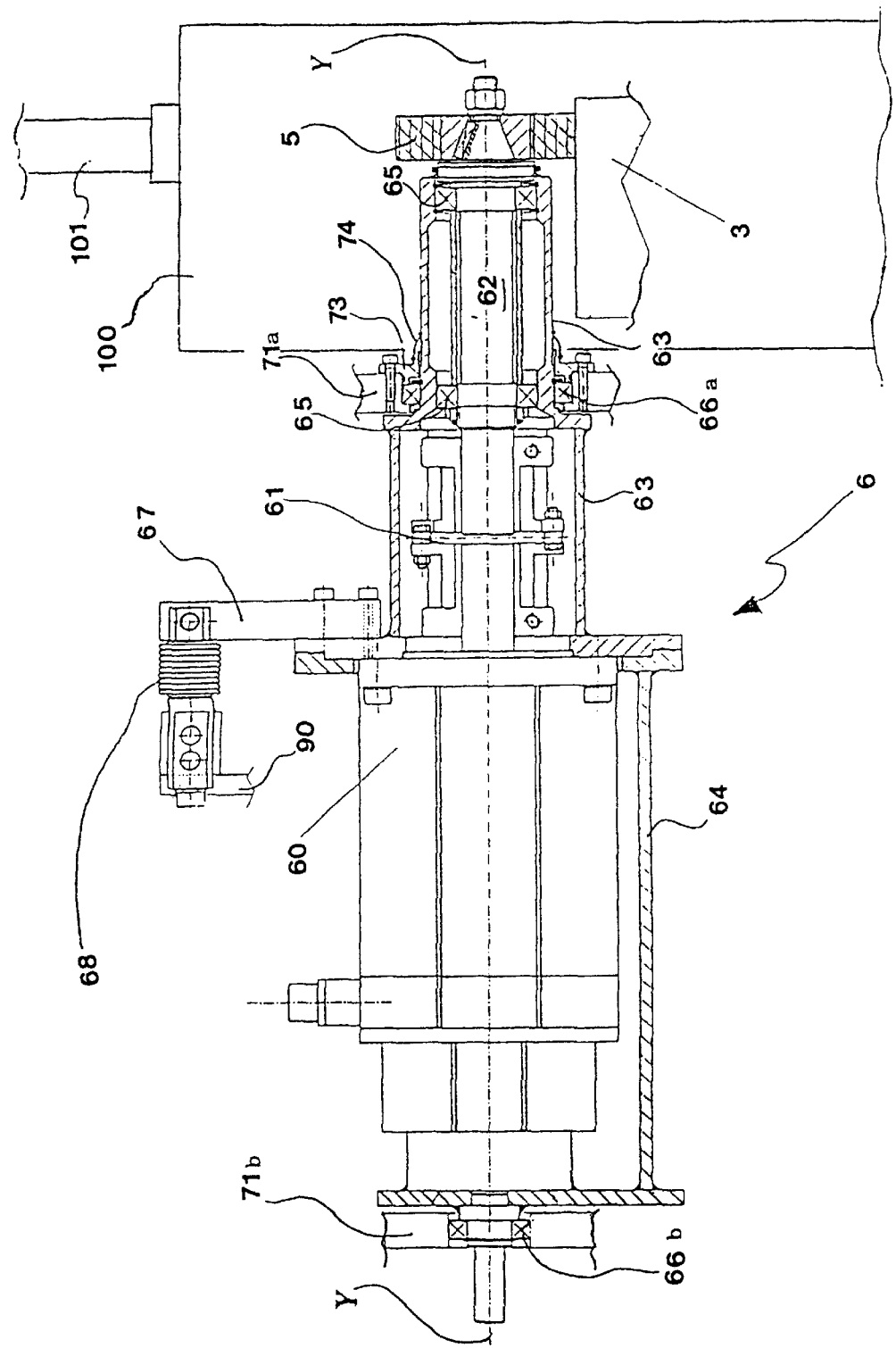
FIG. 4 shows a detail of the apparatus according to the preceding figures.

The driving group 6 of the specimen 5 is shown in detail in FIGS. 2, 3 and 4.

This group also comprises an electric motor 60 of the brushless type which is connected at the output by means of a joint 61 to a spindle 62, at the end thereof the specimen 5 is mounted.

As can be seen from FIG. 4, the joint 61 and the spindle 62 are housed inside a closed cylindrical casing 63 which, at its end opposite to that where the specimen 5 is located, is joined to a cradle seat 64 where the electric motor 60 is located, forming a single rigid body therewith.

The motor 60 is fixed to the inner walls of the cradle-type seat which, being open at the top, facilitates ventilation thereof; the spindle 62 on which the specimen 5 is mounted is however supported inside casing 63 so as to rotate freely about axis Y, by means of two bearings 65.

The rigid body formed both by the casing 63 and the cradle seat 64 is free to rotate about the axis Y owing to two low-friction bearings 66a, 66b, one of which is arranged at the furthest end from the specimen 5 and the other coaxially with one of the bearings 65 which support the spindle 62 inside the casing 63.

The cradle seat 64 also has, mounted on it, an arm 67 radially protruding over a predefined length and bearing, on its free end, a load cell 68 in the form of a strain gauge intended to detect the forces which act with respect to the axis Y.

Basically, since the length of the arm 67 is known, the forces measured by the cell following the small rotations of the cradle 64 (and the casing 63) caused by the motor 60 fixed on it, may be easily converted into a torque value by multiplying it for the known length of the arm 67.

Of course, this will be true for rotations of a magnitude (of the order of 0.001 radians) such that the non-linearity of the displacements at the end of the arm 67 on which the cell 68 is mounted, does not affect the correct operation of the latter.

It must also be pointed out that, in accordance with a preferred embodiment, the load cell 68 is of the prestressed type so as to eliminate imprecision in the measurements caused by any play between the cell itself and the support arm.

The driving group of the specimen 5 described above is supported by the structure 2 in a balanced manner owing to an assembly system which is described below.

The body formed by the casing 63 and the cradle seat 64 is mounted on a frame which comprises a longitudinal member 70 extending parallel to the axis Y and two plates 71a, 71b, which are transverse to the longitudinal member and are fixed to the end thereof: the bearings 66a, 66b supporting the abovementioned body are respectively mounted in these plates.

For mounting of the bearing 66a in the front plate 71a, namely that associated with the casing 63 where the spindle 62 is housed, a bush 73 is provided, being fixed on the front of the said casing by means of screws (see FIG. 4).

In order to protect this bush against water, dust and the other agents used during the tests performed with the apparatus 1, a seal 74 is provided in this example. Said seal consists of a sleeve which is made of rubber or other equivalent material and is fitted around the casing 63 and the part of the bush 73 adjacent thereto.

The weight of the operating group 6 and the associated support frame is balanced by a counterweight 75, the position thereof along a graduated rod 76 is varied manually by means of a handwheel 77 associated with an actuating screw 78.

More specifically, the longitudinal member 70 together with the plates 71 which support the driving group 6 are supported by a bridge 80 of the supporting structure 2 of the apparatus.

For this purpose the longitudinal member 70 is provided longitudinally with a tenon guide 81 slidably engaged with two mortise clamps 82 which are fixed to the bridge 80.

The latter also has, mounted on it, a motor 85 with an associated reduction gear for actuation of a screw 86, with which a cursor 87 rigidly connected to the longitudinal member 70 is associated (see FIG. 2); three proximity switches for stopping the cursor in corresponding positions indicated by A, B and C in the drawings are located above the screw 86.

On the opposite side, the cursor 87 is integral with the graduated rod 76 on which the counterweight 75 moves.

As can be seen from the drawings, a bracket 90 is also bolted onto the longitudinal member 70 and serves as an element for connecting the load sensor 68 to the frame which supports the operating group 6 of the specimen.

The apparatus in this example is provided with a vibration damping device comprising a lever 91 which is fixed at one end to the bridge 80 and which has, mounted on its opposite end, a viscous damping device 93 consisting of a disk 94 movable inside a cylindrical chamber 95.

As can be seen from FIG. 1, the road drum 3 and the specimen 5 of the apparatus 1 are located inside a chamber 100 to which the various nozzles 101 for supplying water and other materials used during the tests are fitted (in FIG. 1 only one of said nozzles has been shown for the sake of simplicity).

By way of completion of the description provided above it must be added that, from a functional point of view, the two electric motors 40 and 60 are controlled so as to allow the possibility of setting the desired ratio between the speed of rotation of the road drum 3 and of the specimen 5, depending on the type of tests which are to be performed (pure rolling, positive or negative slipping, etc.).

More specifically, the aforementioned motors are operationally linked to each other; this is made possible by the fact of having used electric motors of the type which can be controlled electronically, such as in particular brushless motors.

Advantageously in this case the motor 40 of the road drum is the master motor, while the motor of the specimen 5 is the slave so that the respective speeds of rotation have a relative ratio selected depending on the type of control which has been set.

Preferably this ratio may vary from 0 to infinity: in other words, all the setting conditions ranging between a first limit situation (road drum rotating/specimen at a standstill) to the opposite limit situation (road drum at a standstill/specimen rotating) are possible.

Preferably, the road drum has only one direction of rotation, i.e. clockwise or anti-clockwise, while the specimen may rotate in both directions.

In combination with or as an alternative to the speed of rotation, it is also possible to link the position (i.e. the angle corresponding to the rotation performed) of the specimen motor to that of the road drum motor.

Preferably, the sensors used in the apparatus are absolute or incremental encoders.

Basically, therefore, the transmission ratio of the two spindles which actuate the road drum and the specimen will be determined by the setting of the two motors 40 and 60.

Obviously, for its operation, the apparatus 1 is provided with a central electronic control unit (FIG. 1 shows partially the wiring for connection to this unit) which performs the function of adjusting the operating parameters (voltage, current, etc.) of the motors so as to perform the desired test cycles.

In this connection it must be pointed out that with the apparatus according to the invention it is possible to perform complex test cycles such as, for example, those with automatic reversal of the slipping movement between specimen and road drum (from positive to negative and vice versa), those with periodic variation of the said slipping movement, or those with application of a predefined torque on the specimen and the like.

These important results are made possible owing to the use of motors which are operationally linked to each other and can be electronically controlled, as in the case of the brushless electric motors mentioned.

Operationally speaking, the apparatus described above is therefore programmed at the start of each test cycle so as to perform the various operating steps required.

The road drum 3 and the specimen 5 are then made to rotate by the respective groups 4 and 6 depending on the input signals processed by the electronic control means mentioned above.

In this way the various tests (rolling test, slipping test, test with application of the set torque, etc.) are performed and the experimental variables such as the force existing between the specimen and the road drum, the increase in the surface temperature of the rubber, the speed, and the like, are measured.

These tests may be performed in dry, wet and mixed conditions as well as with different surface roughness owing to the special configuration of the road drum, the external surface of which is divided up into different circumferential bands, and owing to the possibility of moving the specimen 5 tangentially with respect thereto.

In this connection it may be noted how operation of the motor 85 produces the displacement of the cursor 87 along the screw 86, into one of the predefined positions A, B and C; since the cursor is rigidly fixed to the longitudinal member 70, it moves integrally therewith together with the driving group 6 of the specimen 5. It should be noted how, during this operation, the movement of the longitudinal member is guided by the engagement between the tenon guide 81 thereof and the mortise clamps 82 arranged on the bridge 80.

Following displacement, the specimen moves forwards or backwards along the contact generatrix of the road drum, as indicated by the arrow in FIG. 2, thus interacting with the zones of varying roughness situated thereon.

From the description provided hitherto it is therefore possible to appreciate how the present invention achieves the object set out before.

This is to be attributed to the particular supporting system of the motor 60 and spindle 62, which are arranged inside the body formed by the cradle seat 64 together with the casing 63 thereby making it possible to avoid the sealed bearings associated with the specimen actuating spindle, which were the source of harmful friction in the prior art.

In this way, indeed, the spindle 62 is housed inside a closed casing and is therefore protected from the water which is sprayed toward the specimen zone; consequently, the bearings 65 on which the spindle is rotatably mounted in this casing may be of the conventional, i.e. the non-sealed type.

The bearing 66a which supports the casing 63 in the region of the front plate 71a may, on the other hand, be protected by the bush 73 and by the sleeve 74 because the casing 63 does not rotate in the manner of the spindle 62, since it performs only minimum oscillations of the order of a few thousandths of a radian (detected by the load sensor 68).

The protection of this bearing is therefore facilitated by this fact.

In other words, in the apparatus according to this invention, the fact of having arranged the spindle 62 inside a closed housing allows to avoid moving external parts which could be exposed to water and to the other agents used during the tests: this eliminates therefore the need to have sealed bearings for the spindle and facilitates instead the application of systems for protecting the low-friction bearings which support the casing 63.

Obviously variations of the invention with respect to the example thereof described herein may be envisaged.

Firstly it must be pointed out that the parts which support the operating group 6 of the specimen 5 may be different from the frame formed by the longitudinal member 70 and the plates 71; the important thing, of course, is that this group may be displaced along the axis Y as described above and is free to rotate with respect to this axis.

Furthermore, the systems for operating the specimen and the road drum may be of the most varied kind with motors of various types, provided that they are able to offer the same features with regard to the possibility of performing adjustment necessary for the tests mentioned.

Similarly, the methods of supporting and moving the operating group 6 of the specimen, i.e. the frame formed by the longitudinal member 70 and the plates 71, as well as the mechanism with the motor 85, the screw 86 and the cursor 87, may be replaced by equivalent mechanical solutions which are within the task of a person skilled in the art.

These and other variations will however fall within the scope of the claims which follow.

What is claimed is:

1. Apparatus for testing tire compounds, comprising:
    a road drum;
    a specimen, the road drum and the specimen rotating about respective parallel axes X and Y and being in rolling contact with each other; and
    a driving mechanism for rotation of the road drum and the specimen, the driving mechanism comprising a specimen driving group in which a spindle is driven by a motor, wherein the spindle is rotatably housed in a casing and rotatably mounted on a non-sealed spindle bearing and wherein the motor is fixed in a cradle seat integral with the casing so as to form a rigid body therewith, the body being supported in an idle manner with respect to the Y axis of rotation of the specimen and being free to rotate about said Y axis.

2. Apparatus according to claim 1, wherein the body formed by the casing and by the cradle seat is supported so as to be able to perform a translatory movement along the Y axis of rotation of the specimen.

3. Apparatus according to claim 1, wherein the body formed by the casing and by the cradle seat is supported on a front bearing arranged on the casing and a rear bearing arranged at the end of the cradle seat opposite to the specimen, where at least the front bearing is associated with a rubber protection sleeve.

4. Apparatus according to claim 1, wherein an arm projecting radially with respect to the Y axis of rotation of the specimen is present on the body formed by the casing and the cradle seat, said arm having a load cell associated with it.

5. Apparatus according to claim 1, wherein the operating group of the specimen is mounted on a frame which comprises a longitudinal member parallel to the Y axis of rotation of the spindle and two plates transverse thereto, which is slidable along this axis and is balanced by a counterweight.

6. Apparatus according to claim 1, wherein the driving group of the road drum and the driving group of the specimen comprise a respective electric motor of the brushless type.

7. Apparatus according to claim 6, wherein the motor driving the specimen is operationally dependent on the motor driving the road drum in at least one of the following: position setting and speed setting.

8. Apparatus according to claim 1, comprising a device for damping the vibrations of the driving group of the specimen.

9. Apparatus according to claim 8, wherein the vibration damping device comprises a lever having one end connected to a bridge of the supporting structure of the apparatus on which the operating group of the specimen is mounted, and the other end being associated with a disk oscillating in a viscous damping chamber.

\* \* \* \* \*

UNITED STATES PATENT AND TRADEMARK OFFICE
CERTIFICATE OF CORRECTION

PATENT NO.   : 6,591,669 B1
DATED        : July 15, 2003
INVENTOR(S)  : Antonio Serra et al.

It is certified that error appears in the above-identified patent and that said Letters Patent is hereby corrected as shown below:

Title page,
Item [57], ABSTRACT,
Delete in its entirety and insert therefor:
--An apparatus for testing tire compounds includes a road drum and a specimen, each rotating about respective axes X and Y, and each being in rolling contact. The specimen of rubber to be analyzed is mounted at the end of a spindle operated by a motor. The spindle is housed inside a closed casing so as not to be exposed to water or other agents during tests. This results in an apparatus wherein the spindle driving the specimen may be supported by non-sealed and hence low-friction bearings, thereby not altering the results of the tests carried out.--.

Signed and Sealed this

Fifth Day of April, 2005

JON W. DUDAS
*Director of the United States Patent and Trademark Office*